United States Patent [19]

Siczek et al.

[11] Patent Number: 5,526,394
[45] Date of Patent: Jun. 11, 1996

[54] DIGITAL SCAN MAMMOGRAPHY APPARATUS

[75] Inventors: Bernard Siczek, Boulder, Colo.; Emre Toker, Tucson, Ariz.

[73] Assignee: Fischer Imaging Corporation, Denver, Colo.

[21] Appl. No.: 157,992

[22] Filed: Nov. 26, 1993

[51] Int. Cl.[6] .................................................. A61B 6/04
[52] U.S. Cl. ..................... 378/37; 378/145; 378/98.8; 378/156
[58] Field of Search .......................... 378/62, 37, 98.3, 378/98.8, 146, 151, 157, 193, 189, 147, 151, 156

[56] References Cited

U.S. PATENT DOCUMENTS

| | | | |
|---|---|---|---|
| 4,096,391 | 6/1978 | Barnes | 250/505 |
| 4,157,572 | 6/1979 | Kennedy et al. | 360/33 |
| 4,179,100 | 12/1979 | Sashin et al. | 250/416 |
| 4,203,037 | 5/1980 | Gur et al. | 250/505 |
| 4,692,937 | 9/1987 | Sashin et al. | 378/62 |
| 4,696,022 | 9/1987 | Sashin et al. | 378/41 |
| 4,744,099 | 5/1988 | Huettenrauch et al. | 378/157 |
| 4,946,238 | 8/1990 | Sashin et al. | 350/96.27 |
| 4,998,270 | 3/1991 | Scheid et al. | 378/37 |
| 5,142,557 | 8/1992 | Toker et al. | 378/37 |
| 5,289,520 | 2/1994 | Pellegrino et al. | 378/208 |
| 5,335,257 | 8/1994 | Stunberg | 378/37 |

OTHER PUBLICATIONS

Yaffe, "Digital breast techniques excel at image display", Diagnostic Imaging, May, 1993, pp. 79, 80, 82 85 and 105.
Jackson et al., "Imaging of the Radiographically Dense Breast", Radiology, Aug., 1993, pp. 297–300.

*Primary Examiner*—David P. Porta
*Assistant Examiner*—Don Wong
*Attorney, Agent, or Firm*—Sheridan Ross & McIntosh

[57] ABSTRACT

An apparatus is disclosed for imaging a patient's breast (18) by scanning an imaging signal (58) and a receiver (30) across the patient's breast (18) and then constructing a time-delay integration composite image based on the scan. The receiver (30) includes an array of radiation sensitive detector elements (132). Read out of the array (132) is synchronized with the scanning motion of the receiver (30) based on output from position encoder (104) such that synchronization is maintained despite scan drive variances. A novel assembly (106) is also disclosed for allowing selection of an appropriate radiation filter based on particular imaging conditions.

27 Claims, 6 Drawing Sheets

DIGITAL SCAN MAMMOGRAPHY APPARATUS

FIELD OF THE INVENTION

The present invention relates generally to digital mammography and, in particular, to an improved apparatus for imaging a selected region of a patient's body by scanning an imaging signal across the region and constructing a composite image of the region based on the scan. The invention has particular application to the field of mammography.

BACKGROUND OF THE INVENTION

Breast imaging is considered the most demanding of medical imaging procedures. With regard to spatial resolution, breast imaging specialists are now commonly interested in imaging lesions or masses that may require an imaging aperture that is about 50 microns in size or less. Contrast requirements are also demanding because lesions or masses to be visualized sometimes have x-ray absorption characteristics similar to that of the surrounding tissue. In this regard, 12 bit contrast resolution, corresponding to about 4000 distinguishable shades between black and white in the resulting image, is often desired.

X-ray mammography is the most sensitive breast imaging modality currently available and is widely used in detecting and diagnosing the nature of small non-palpable breast lesions. Both film-based and digital systems are currently available for breast imaging. In film-based systems, x-rays are transmitted through the patient's breast and impinge upon a phosphor screen. Light emitted from the phosphor screen as a result of the absorption of x-rays is detected by light sensitive film. The film is then developed to yield an image of the patient's breast which can be viewed on a light box. In digital systems, a radiation receiver is used in place of the film. The receiver yields an electronic signal which can be digitally processed for viewing on a high resolution monitor. Currently, only limited field of view digital systems, e.g., 5 cm by 5 cm field of view systems, approximate film based systems in mammographic performance.

Heretofore, film-based systems have been most commonly used for breast imaging and improvements over the years in film-based, x-ray imaging technology have resulted in improved imaging capability and reduced radiation dosage. Film based systems are, however, subject to certain limitations. For example, film granularity and film screen noise limits the spatial resolution of the resulting image. Moreover, films which provide higher resolution images generally require greater radiation doses. In addition, in film-based systems, the resulting image contrast can be significantly affected by scattered radiation. Although the effects of scattered radiation may be reduced by using an antiscatter grid, grids necessitate a greater radiation dosage. Furthermore, the time required to develop film images renders film-based systems less desirable for some applications.

Recently, researchers have recognized that digital imaging systems offer potential advantages over film-based imaging systems. In particular, digital imaging systems avoid the problems of film granularity and film screen noise and are theoretically capable of providing outstanding image resolution. Additionally, in digital imaging systems, once the receiver imaging data has been stored, various processing and display parameters can be manipulated to optimize the displayed image. Digital systems also allow for substantially real-time imaging as may be desired. The stored digital imaging data can also be downloaded for transmission within a computer network and retrieved at remote workstations thereby facilitating information storage, consultation and computer image analysis.

However, current and proposed digital imaging systems for use in mammography do not fully meet the needs of the industry. Digital imaging has been effectively used in the context of stereotactic localization of breast lesions for subsequent needle biopsy procedures. However, such systems are not intended for full field breast imaging and are normally used only to image a relatively small area of the breast where the lesion is located, e.g., a 5 cm by 5 cm window. Expanding such digital imaging systems for full field, single exposure breast imaging would be complicated and expensive due to the high degree of spatial resolution required for imaging small, non-palpable breast lesions. Moreover, such a full field, single exposure imaging system would be affected by scattered radiation. That is, the receiver of such a system would receive significant scattered radiation from the patient's breast in addition to the desired, image-forming x-ray signal. Additionally, use of a grid to reduce the effects of such scattered radiation would necessitate a greater dosage. As a result, subtle breast lesions could be obscured or difficult to ascertain, even with digital processing and display enhancements.

SUMMARY OF THE INVENTION

The present invention provides an improved digital mammography apparatus which allows for high resolution, full field breast imaging. In addition, the present invention reduces the effects of scattered radiation without requiring the use of a dose-inefficient grid. The present invention also provides a novel mechanism for acquiring image information as a receiver is scanned across an area of interest and integrating the acquired information to yield a high fidelity composite image of the area of interest. Moreover, the present invention allows for automatic selection of a radiation filter so that the filter can be selected based on particular imaging conditions to enhance the resulting image. Furthermore, the present invention allows for utilization of different filters, with different performance characteristics, during the acquisition of a single image of an area of interest so that the filtering characteristics can be separately optimized for portions of the area of interest.

In accordance with one aspect of the present invention, an area of interest within a patient's breast is imaged by transmitting a beam of radiation through the patient's breast, scanning a receiver across the area of interest such that the receiver receives the beam over the course of the scan and processing the resulting information to construct a composite image of the area of interest. The area of interest may comprise a section of the patient's breast or the entire breast volume. In order to conduct the scan, the beam and the receiver can be synchronously moved across the area of interest. In principle, beams of various shapes can be utilized, however, beam shapes having a narrow width and a length at least as great as the chest wall-to-nipple length of the patient's breast (e.g., a fan beam) advantageously provide for both rapid imaging and simplified image processing.

Movement of the receiver is preferably performed across the patient's chest (from side-to-side relative to the patient's breast) rather than transverse to the patient's chest wall (outward from the base of the patient's breast or vice versa)

so that the scan is not interrupted by the chest wall, thereby facilitating a smooth scanning motion across the entire breast for enhanced imaging. The receiver output is processed to provide time delay integration (TDI) image acquisition thus yielding an image with improved signal to noise ratio.

This scanning/TDI technique has a number of advantages over single exposure imaging. For example, in accordance with the present invention, an array of radiation sensitive elements or pixels generally corresponding to the beam cross-section, as opposed to a full field array or a line detector with a single element, can be utilized, thereby simplifying receiver design. In addition, radiation scatter problems are reduced as scattered radiation will generally travel outside of the radiation beam and, therefore, will not be detected. An improved signal-to-noise ratio is thereby achieved. Moreover, this reduction in the effect of scattered radiation can be achieved without increased radiation dosage to the patient because only a portion of the breast needs to be exposed to radiation at any one time. The present invention also allows for breast scanning which readily accommodates women of different sizes and compositions due to patient-specific selection of optimum input x-ray spectrum, the wide dynamic range of the detector, and apparatus geometry.

In accordance with another aspect of the present invention, a position encoding apparatus is provided so as to synchronize receiver read out with the scanning motion so as to yield a high fidelity composite image. The receiver preferably comprises a detector array including at least one row of radiation sensitive elements or pixels corresponding to a lengthwise slice of the patient's breast. The radiation sensitive elements may directly detect the imaging signal, e.g., x-rays, or a secondary radiation device, such as a phosphorescent screen or the like, which emits light upon excitation by the imaging signal, can be interposed between imaging signal source and the detector array. Where a secondary radiation device is employed, the device can be optically coupled to the detector array by a lens, fiber optics, or any other suitable optical components. As the receiver is scanned across the patient's breast, the electrical charge accumulated by the detector array is rapidly read out so as to obtain imaging information corresponding to a series of lengthwise slices of the patient's breast. This information can then be used by a processor to construct a composite image of the area of interest within the patient's breast.

In one embodiment, the receiver comprises a two-dimensional array of radiation sensitive elements, wherein the width of the array is defined by a plurality of lengthwise rows of the elements. As the receiver is scanned across the area of interest within the patient's breast as described above, the accumulated charge or charge packet in each pixel is synchronously shifted from row-to-row such that each such charge packet tracks particular breast information of the area of interest. By selecting an array corresponding to the imaging signal cross-section, charge can be integrated over a time period corresponding to passage of the imaging signal width across a particular location, thereby providing an improved signal-to-noise ratio and maximizing the resulting imaging information for a particular radiation dosage. When a row of charge packets reaches the side of the array, the packets are shifted to an adjacent, light shielded array of pixels and then read out in a conventional fashion, e.g., via a serial register.

In order to accurately construct a composite image based on scan imaging data, it is important to correlate imaging data acquisition to the scanning motion and, in turn, to the position of the patient's breast. In accordance with the present invention, this can be accomplished by mounting the detector array on a positional encoder. The encoder produces a signal, e.g., sequence of electrical pulses, as a function of detector array motion. For example, a linear or rotational encoder may be employed. These pulses can be monitored to trigger charge packet shifting and to determine the precise location of an array element relative to a scan of the patient's breast for use in composite image construction. Because charge packet shifting is referenced to encoder output, synchronization is maintained despite variances in drive speed or other irregularities in detector array motion.

In accordance with a still further aspect of the present invention, an imaging system is provided which allows for selection of an appropriate radiation filter to suit specific imaging conditions. For example, the particular filter selected may depend on the nature of the breast tissue to be imaged (e.g., the density and thickness of the tissue), the operating parameters of the radiation source (e.g., voltage, current, anode material, focal spot size) or other factors. The imaging system includes: an imaging signal source; an imaging signal receiver disposed opposite the source with the breast positioned therebetween; a support structure, disposed between the source and the patient's breast, for carrying two or more filters having different performance characteristics; and a selection device for positioning a selected filter in a path of the imaging signal. The filter can be directly selected by the user or the filter can be selected by a control device based on input information or feedback relating to particular imaging conditions. In the case of a scanning system as described above, such feedback can further be used to vary the operating parameters of the radiation source during a scan, for example, to change photon flux as glandular tissue is encountered so as to optimize imaging quality.

In accordance with yet another aspect of the present invention, an imaging system is provided which allows for use of different filters, having different filtering characteristics corresponding to different portions of an area of interest within a patient's body, during acquisition of a single image. The system comprises: an imaging signal source and an imaging signal receiver disposed in opposing relationship with the area of interest positioned therebetween; and a filter support structure for supporting at least a first filter in a first position relative to the imaging signal source corresponding to a first portion of the area of interest, and for supporting a second filter, different from said first filter, in a second position relative to said imaging signal corresponding to a second portion of the area of interest. In this manner, the filtering characteristics can be optimized on an area by area basis for a single image. For example, a clinical problem associated with breast imaging is that the retroglandular area (posterior part of the breast) is typically composed of fatty tissue while the anterior part is fibrous and glandular. This problem can be addressed in accordance with the present invention through selection of an appropriate filter pair.

Although the present invention is specifically described herein with respect to breast imaging applications, it will be appreciated that various aspects of the present invention can be utilized in connection with imaging other body regions.

BRIEF DESCRIPTION OF THE DRAWINGS

Additional aspects and features of the present invention and corresponding advantages thereof will be appreciated upon consideration of the Detailed Description below, taken in conjunction with the Drawings, in which.

DETAILED DESCRIPTION

Figure 1:
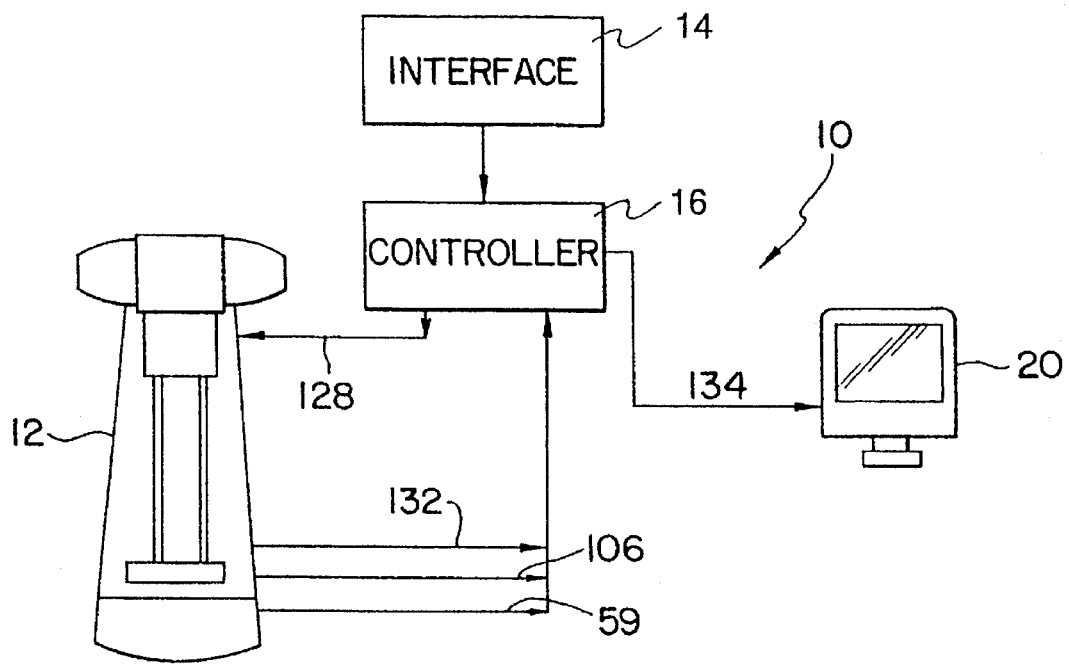
FIG. 1 is a schematic diagram of an imaging system constructed in accordance with the present invention.

Referring to FIG. 1, an imaging system constructed in accordance with the present invention is identified by the reference numeral 10. Generally, the system 10 includes: a digital scan imaging device 12; a user interface 14, which may comprise a computer keyboard, for allowing the user to direct operation of the system 10; a controller 16, such as a computer, for operating the imaging device 12 and processing imaging information to construct a composite image of the patient's breast; and a monitor 20 for displaying the composite image.

Details of the imaging device 12 are shown in FIGS. 2–8. The imaging device 12 includes an imaging signal source 28 such as an x-ray tube, an imaging signal receiver 30 such as a digital camera, a compression assembly 32 for compressing and immobilizing the patient's breast 18, a scanning assembly 34 for scanning the imaging signal across the patient's breast 18 and related components supported on a pedestal 36.

In the illustrated embodiment, the source 28, receiver 30 and portions of the compression assembly 32 and scanning assembly 34 are rotatably mounted on pedestal 36 via shaft 38 and bearings 40 so as to allow for different approach angles for imaging the patient's breast 18, i.e., these components can be rotated about the patient's breast 18 in a direction generally parallel to the patient's chest wall to attain a desired initial or reference position for the imaging scan. Once such a desired position is attained, these components can be locked into position by brake 42. The brake 42 can comprise, for example, a nonrotatable gear section 44 which meshingly engages corresponding gear teeth provided on shaft 38 so as to lock the shaft 38 in place. The gear section 44 can be engaged or disengaged as desired via an electromechanical clutch which can comprise a solenoid actuator.

The compression assembly 32 compresses the patient's breast 18 to a more uniform thickness and concomitantly immobilizes the patient's breast to enhance the resulting image. As shown, this is accomplished by compressingly engaging the patient's breast 18 between the fixed upper surface 46 of housing 48 and the compression paddle 50 which is moveable along rails 52. It will be appreciated that paddle 50 and upper surface 46 are formed from x-ray transparent materials. The paddle 50 can be manually moveable or motor driven. As shown, the paddle 50 is driven by compression motor 54, e.g., an electromechanical servo motor, via appropriate linkage including shaft 56 which is located to avoid interference with the scanning assembly 34 as will be understood from the description below. A conventional release mechanism (not shown) is provided to allow for rapid release of the patient's breast 18 from compression in case of emergency.

Figure 5:
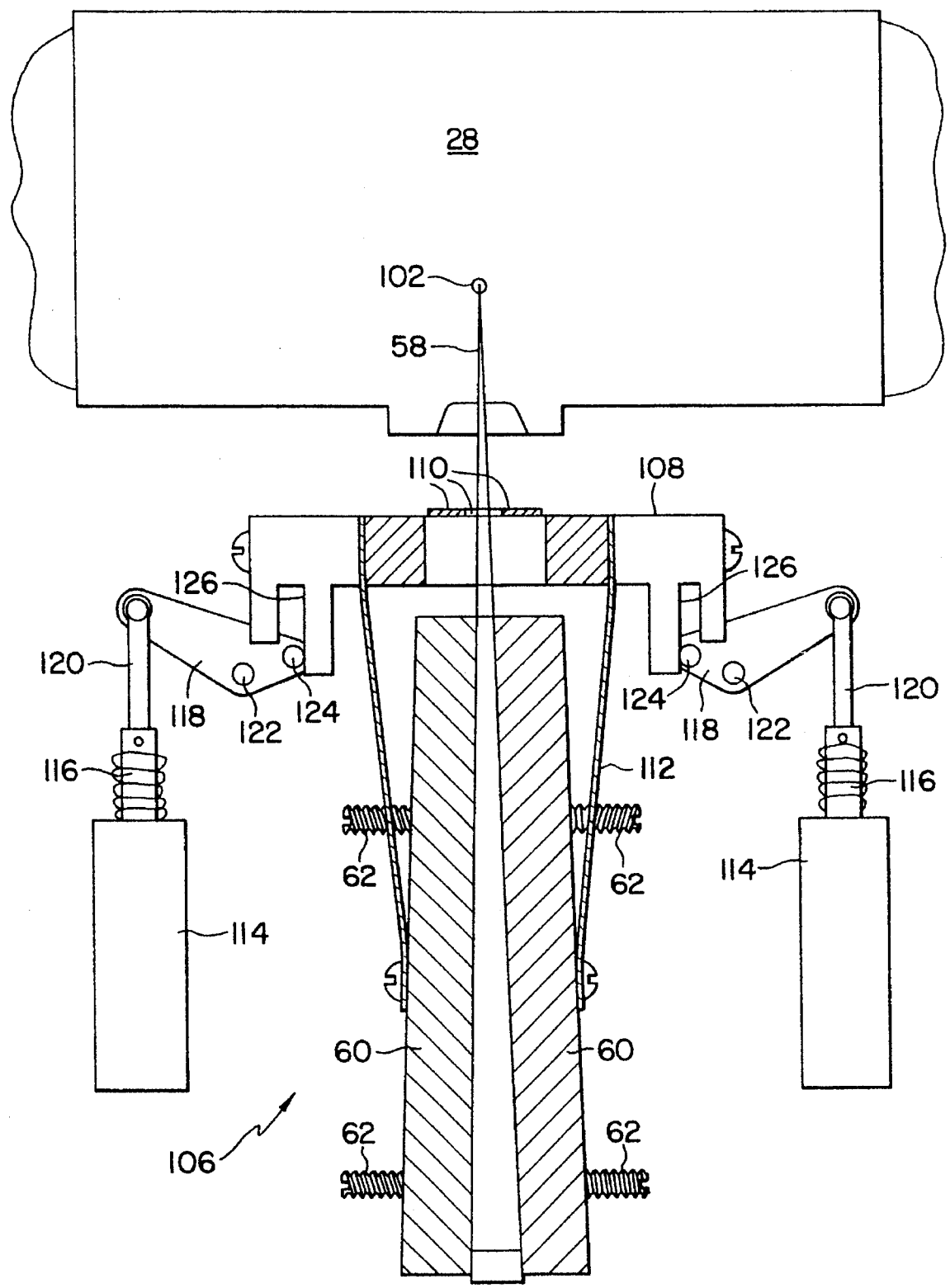
FIG. 5 is a front, cross-sectional view showing the filter selection assembly which is incorporated into the device of FIG. 2.

The patient's breast is imaged by scanning an imaging signal 58 across the patient's breast 18 and using the receiver 30 to obtain imaging information during the scan. The illustrated imaging signal 58 comprises a narrow x-ray fan beam transmitted by source 28 through x-ray absorbent collimator plates 60 (FIG. 5). The spacing of collimator plates 60 can be adjusted by screws 62 to control the width of signal 58. In addition, the width of the signal 58 can be controlled by providing lead slots, positioned upstream and downstream from the patient's breast 18. Although signals of various widths can be used for imaging, a narrow, collimated beam can reduce x-ray dose and the effects of scattered radiation. In addition, the illustrated signal 58 has a depth, D, at least as great as the chest wall-to-nipple depth of the patient's breast 18. Although lesser signal depths could be employed, the illustrated signal 58 allows for single pass, full field scanning, thereby enhancing imaging speed and simplifying processing.

The receiver 30 receives the imaging signal 58 and transmits information, generally indicated by arrow 59 in FIG. 1, to the controller 16 based on the received signal 58. The receiver 30 may comprise any of a variety of digital cameras. In this regard, the receiver 30 can include an x-ray sensitive receiver for directly detecting an x-ray signal or phosphorescent screens which emit light upon excitation by x-ray radiation. Where phosphorescent screens are employed, lens based optics can be utilized to focus the emitted light on the focal plane of the imaging camera or fiber optics can be employed.

The illustrated receiver 30 comprises a camera including a row of phosphorescent screens 64 arranged to generally match the signal 58 cross-section. The screens 64 are coupled via tapered fiber optic reducers 66 to an array 132 of pixels such that each pixel is mapped to a corresponding screen location. The pixels can thus be read out as described below to yield an electronic signal which can be processed to provide an image of the patient's breast. The camera is moved in synchronization with the signal 58 during scanning as will also be described below.

The scanning assembly 34 includes a scanning motor 68, e.g., an electromechanical servo motor, for co-driving pivotal motion of the source 28 and synchronous scanning motion of the receiver 30. In the illustrated embodiment, this is accomplished by mounting the source 28 and the receiver 30 on a pendulum 70 which, in turn, is rotatably carried on shaft 72 in alignment with the focal spot 102 of source 28. Power is transmitted from motor 68 via drive belt 74 which is carried by output pulley 76 mounted on output shaft 78 and right transaxle pulley 80 mounted on transaxle 82 which is coaxial with shaft 72. Also mounted on transaxle 82 is left transaxle pulley 84 which carries drive belt 86. Drive belt 86 is carried at its lower extremity by encoder shaft pulley 88 which is mounted on encoder shaft 90.

Figure 6:
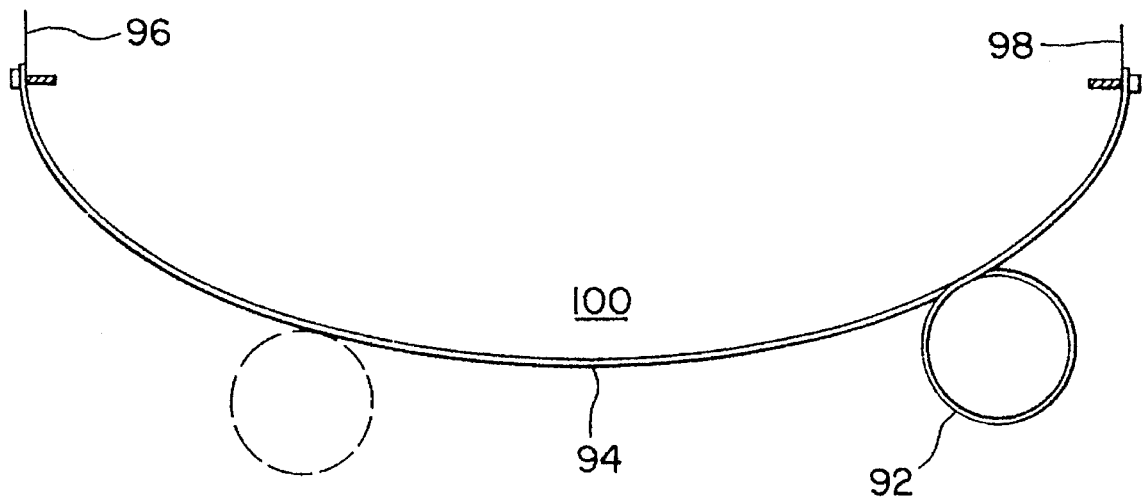
FIG. 6 is a front view showing the steel belt drive mechanism which is incorporated into the device of FIG. 2.
Figure 2:
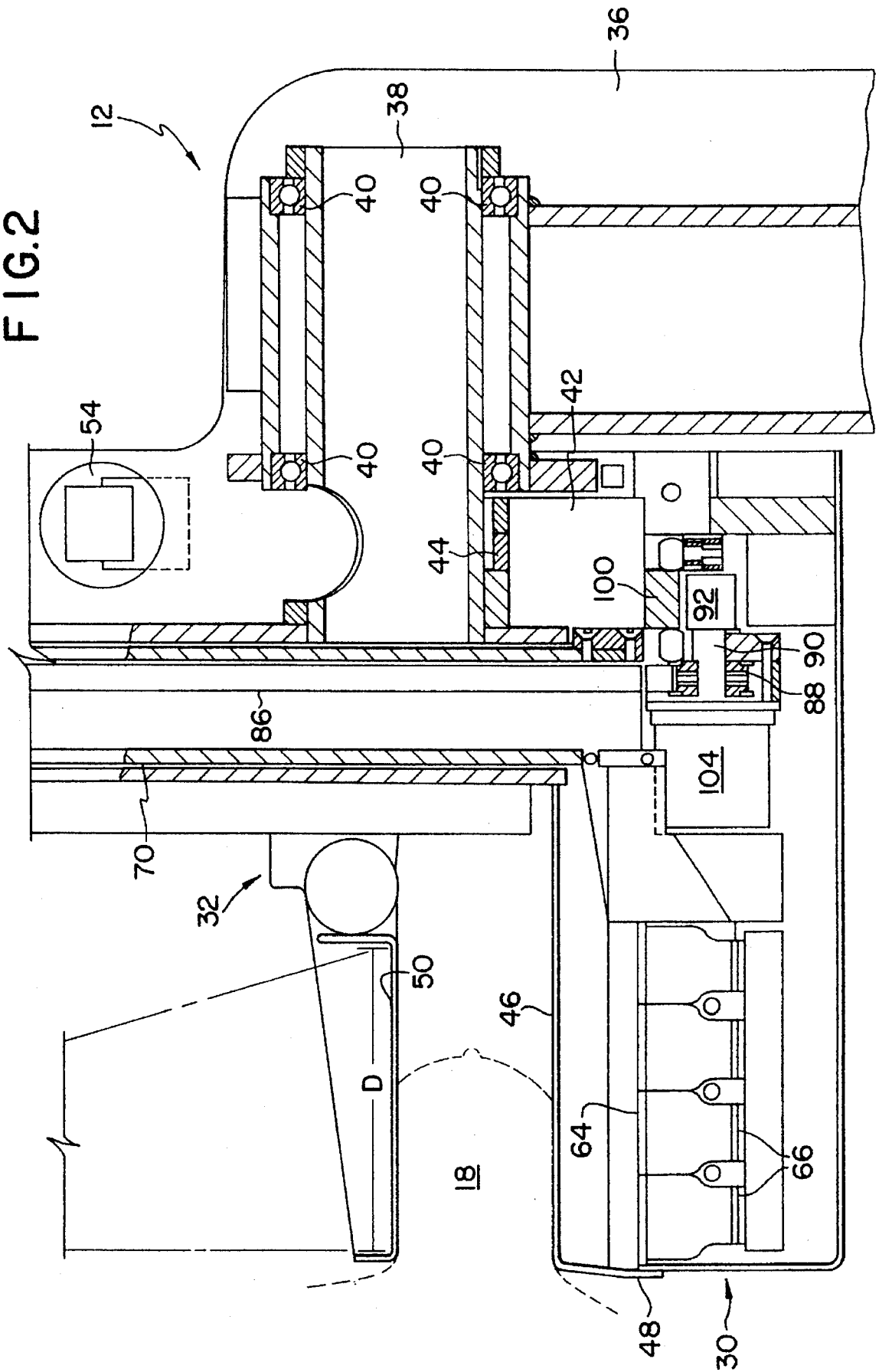
FIG. 2 is a side cross-sectional view showing a bottom portion of an imaging device constructed in accordance with the present invention, which is incorporated into the system of FIG. 1.
Figure 3:
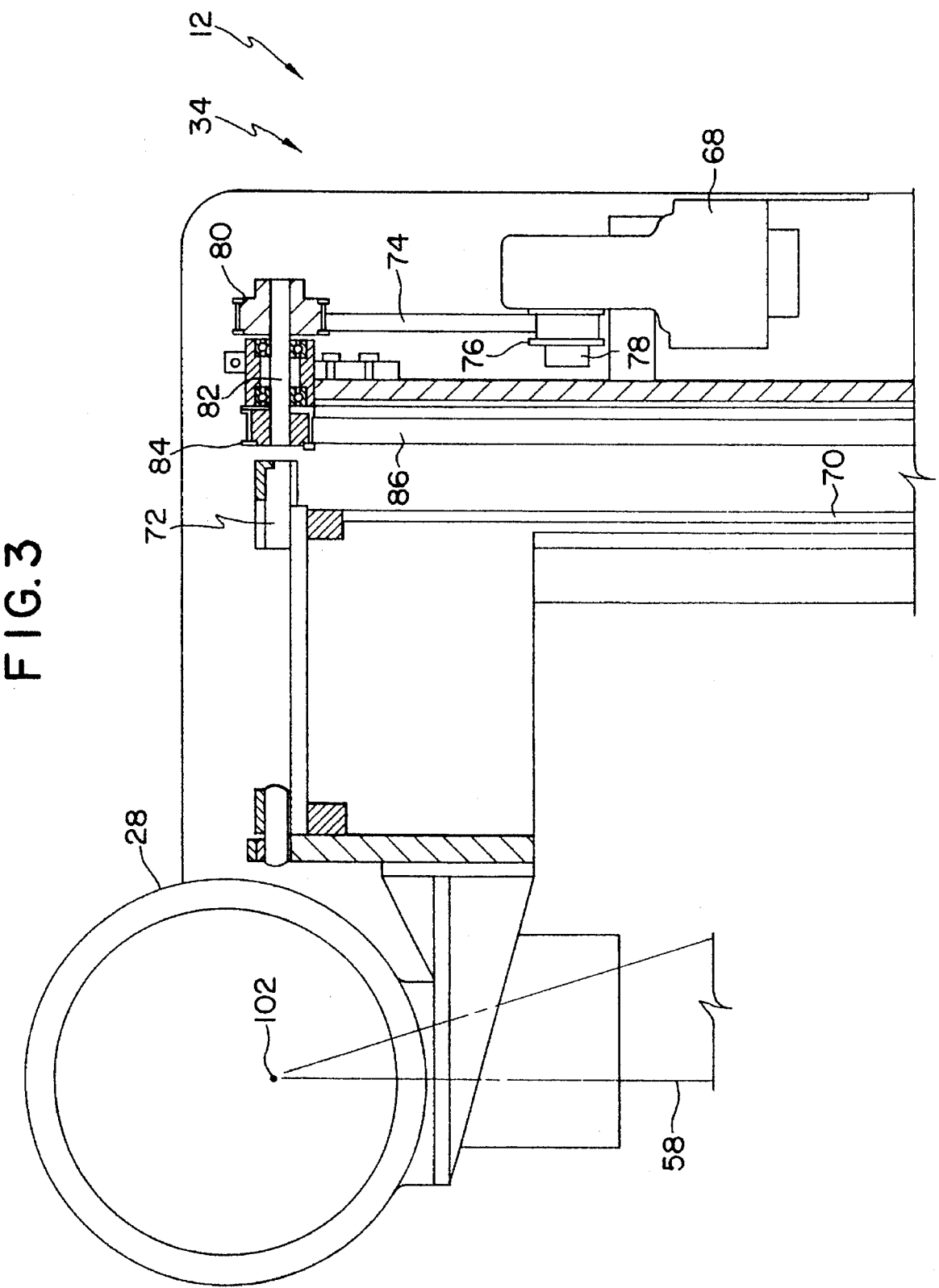
FIG. 3 is a side cross-sectional view showing a top portion of the imaging device of FIG. 2.
Figure 4:
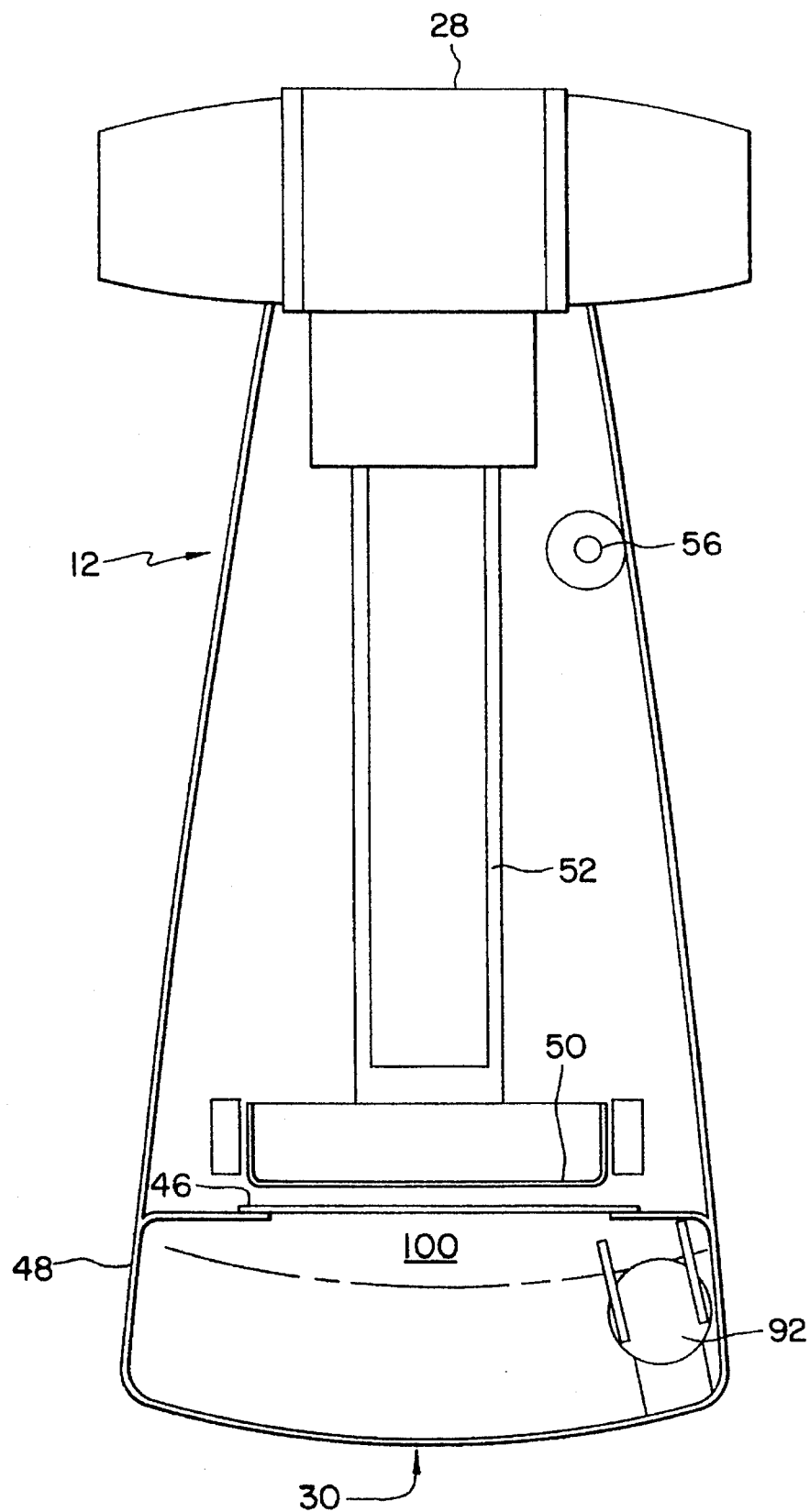
FIG. 4 is a front plan view of the imaging device of FIG. 2.

Steel belt pulley 92 is also mounted on encoder shaft 90 and has a steel belt 94 wrapped therearound as shown in FIG. 6. The steel belt 94, in turn, is attached to the left 96 and right 98 extremities of arcuate cam 100. In this manner, rotation of encoder shaft 90 causes steel belt pulley 92 to take-up and pay-out steel belt 94 such that steel belt pulley 92 pendulantly tracks along cam 100. Because the steel belt pulley 92 is fixed to pendulum 70, this pendulant tracking results in synchronized pivotal motion of source 28 and scanning motion of receiver 30. The illustrated steel belt drive reduces or eliminates backlash associated with start up acceleration and provides a smooth scanning motion thereby enhancing the resulting image.

In order to fully and accurately construct a composite image of the patient's breast 18 based on a scan, it is necessary to frequently read out imaging data so that information regarding the entire area of interest is obtained and to accurately correlate the imaging data to the corresponding receiver/beam locations. This is accomplished in accordance with the present invention by directly correlating positional information regarding the receiver 30 (which also reflects the position of signal 58 as the movement of the source 28 and receiver 30 is synchronized) and using this information for triggering imaging data acquisition and read out. In the illustrated embodiment, an encoder 104 such as a shaft-to-digital converter is mounted on encoder shaft 90. The encoder 104 provides an electrical signal, generally identified by arrow 106 (FIG. 1), indicative of receiver position based on rotation of encoder shaft 90. The signal 106, which can comprise a series of electrical pulses as a function of the scanning motion of the receiver 30, directs operation of the receiver 30 as will be described.

The illustrated receiver 30 includes an array 132 of pixels (FIG. 8) which are coupled to phosphorescent screens 64 via fiber optic reducers 66 as described above such that each pixel is mapped to a corresponding screen location. The pixel array 132 is "M" pixels long and "N" pixels wide, where M and N can be selected based on the total area and desired spatial resolution of the screens 64. In this regard, the area of the screens can be selected to substantially match the cross-section of the fan shaped imaging signal 58, and the spatial resolution is preferably sufficient to allow imaging of objects that may require an imaging aperture that is about 50 microns in size or even smaller.

During a scan of the patient's breast 18, charge packets are synchronously shifted in pixel-to-pixel fashion across the width of the pixel array 132 such that the position of a particular charge packet within pixel array 132 tracks a corresponding location within the patient's breast 18. In this manner, charge is integrated, as a charge packet moves across the pixel array 132, as a function of the imaging signal intensity incident on the associated phosphorescent screen location. When the charge packets reach the side of the pixel array 132, they are transferred, e.g., via a transfer gate, to read out array 134 which may comprise a linear CCD array. The charge packets, and the imaging information contained therein, can then be clocked in a conventional shift register manner from the read out array 134 for processing by controller 116. The controller 116 receives the resulting read out signal and produces a digital signal representative of an image of the patient's breast 18, which image can then be displayed on high resolution monitor 20.

In order to accommodate charge integration as previously described and to produce a high fidelity image of the patient's breast, it is important that the charge shifting across the pixel array 132 be accurately synchronized with the receiver scanning motion relative to the patient's breast 18. In the illustrated system 10, accurate synchronization is achieved by referencing such shifting directly to receiver motion as indicated by the output of encoder 104. As previously noted, the encoder 104 produces a signal, such as a series of electrical pulses, as a function of receiver motion. This encoder output is communicated to a shift control circuit as illustrated schematically in FIG. 8. The shift control circuit can comprise, for example, a three phase shift circuit such as conventionally employed in CCD clocking networks. However, rather than synchronizing the shift cycle relative to clocked pulses, the phase shift circuit of the present invention synchronizes the shift cycle relative to the received encoder output. In this manner, shifting of the array 132 is synchronized with the scanning motion of receiver 30 even when the scanning motion is disturbed by variances in drive speed or other irregularities.

The imaging device 12 also includes a filter selection assembly 106 (FIG. 6). It has been found that the type of filter used, e.g., Aluminum, Molybdenum, Rhodium, Silver, etc., in combination with other operating parameters of the imaging device 12, can be selected based on particular imaging conditions to optimize the resulting image. In particular, different filters may be preferred based on differences in breast thickness and composition or density from one case to another. The filter selection assembly 106 thus allows for automatic filter selection based on particular imaging conditions.

In the illustrated embodiment, the filter selection assembly 106 is used in conjunction with the collimator plates 60. The assembly 106 includes a platform 108 which carries a number of filters 110. In principle, any useful number of filters 110 can be provided. The illustrated embodiment provides three filters 110 (or filter combinations as described below) which is believed to allow for adequate filtering flexibility for a broad range of applications. The platform 108 is mounted on the collimator plates 60 by symmetrically arranged leaf springs 112, which allow for movement of the platform 108 relative to the signal 58 so that any of the filters 110 can be positioned in the signal's path.

Positioning of the platform 108 is actuated by a pair of solenoids 114. The plunger 116 of each solenoid 114 is connected to a lever plate 118 via an arm 120. The lever plates 118, which are pivotally mounted on pins 122, carry pegs 124 near an inner extremity thereof which are received within slots 126 formed on the underside of platform 108. When one of the solenoids 114 is energized, its plunger 116 and the arm 120 connected to it are pulled in causing the lever plate 118 to pivot, thereby moving the platform 108 so that a different filter 110 is positioned in the path of signal 58. The platform positions corresponding to the conditions where the left solenoid is energized, the right solenoid is energized or neither solenoid is energized allow for selection between three different filters 110.

The solenoids 114 are driven by a signal, generally identified by arrow 128 in FIG. 1, from controller 116. In this regard, the user can direct selection of a desired filter by entering an appropriate command, generally indicated by arrow 130 in FIG. 1, into controller 16 via user interface 14, e.g., "SELECT FILTER 1." Alternatively, the controller 16 can direct selection of an appropriate filter 110 based on feedback indicative of breast thickness and composition or density. In the illustrated embodiment, the controller 16 receives feedback from the compression assembly 32 as generally indicated by arrow 132 in FIG. 1. This feedback can be provided via an electrical signal from an encoder, potentiometer or the like incorporated into the drive mechanism of the compression assembly 32 to indicate the position of moveable compression paddle 50. Additionally, feedback regarding the compression pressure may be provided via a pressure sensor, strain gauge or the like associated with compression paddle 50 so as to provide an indication of breast thickness and density or composition.

A further indication of breast thickness and density or composition can be obtained via a test exposure. Specifically, such a test exposure can be performed as follows. After the patient is positioned and compressed, the receiver 30 is positioned at the center of the imaging area and a very short exposure (e.g., 0.1 second) is taken using a standard filter and standard operating parameters. The data acquired in this mode, e.g., a histogram of radiation intensities, together with the compression assembly feedback as described above is then analyzed by the controller 16 as the receiver 30 is moved to one side of the breast to begin a scan (this analysis can be completed in less than about a second). A look-up table of intensities generated with test objects of various thicknesses and beam hardening qualities stored by the controller 16 can be used in conjunction with the exposure and compression assembly feedback 132 to estimate the thickness and composition or density of the breast under examination. This information in turn can be used by the controller to direct selection of an appropriate filter 110.

Feedback information can also be used to instantaneously optimize the operating parameters of the imaging signal source. For example, it is well known that radiographically dense breast tissue requires a higher exposure for optimal imaging. Such a higher exposure can be achieved during a scan by applying a greater photon flux, e.g., by increasing the output voltage of the source while maintaining adequate source current. In operation, a radiographically dense breast region, such as a region of glandular tissue, would be indicated by reduced intensities as measured by the receiver 30. By monitoring such intensities during a scan and employing the controller 16 as described above to manipulate source operating parameters, the operating parameters can be continually optimized over the course of a scan.

Figure 7:
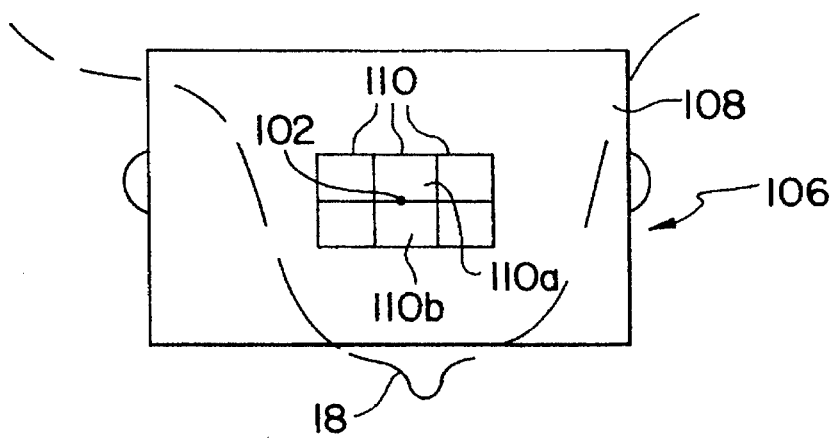
FIG. 7 is a top view showing a filter support structure constructed in accordance with the present invention.
Figure 8:
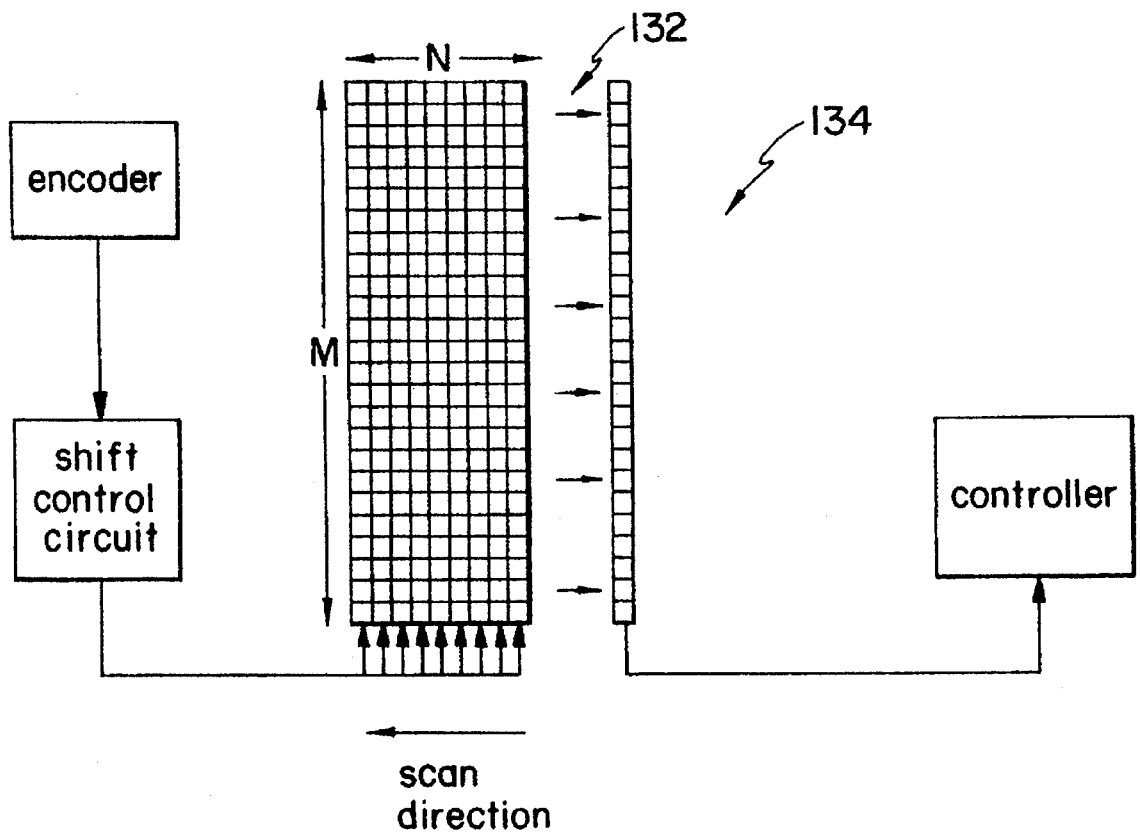
FIG. 8 is a schematic diagram illustrating the control system for reading out the detector array.

Referring to FIG. 7, a top view of the filter selection assembly 106 is shown. As previously noted, platform 108 is moveable so that different filters 110 can be positioned in the path of the imaging signal depending on particular conditions. It is also possible, in accordance with the present invention, to position more than one filter, or a single filter composed of two different materials, in the path of the imaging signal, so that the filtering characteristics can be separately optimized for different portions of the area of interest during a single scan. In this regard, by way of example, the retroglandular area (posterior part of the breast) is normally composed of fatty tissue whereas the anterior part tends to be fibrous and glandular. Accordingly, image quality can be enhanced according to the present invention by positioning different filters in the path of the posterior and anterior portions of the imaging signal. As shown, the platform 108 of assembly 106 carries filter pairs 110a and 110b, where the interface of the filter pairs 110a and 110b is generally aligned with the source focal spot 102.

In summary, in accordance with the present invention, a digital scan imaging procedure is initiated by positioning the patient and operating the compression assembly 32 to engage the patient's breast 18. The user can then direct the controller 16 to select an appropriate filter 110 for the imaging procedure. Alternatively, the controller 16 can direct selection of an appropriate filter 110 based on exposure and/or compression assembly feedback 132. A side-to-side scan of the patient's breast 18 is then performed. At the conclusion of the scan, the controller 16 uses the imaging information 59 obtained in slice-by-slice fashion together with the known receiver position associated with each such slice to construct a composite image of the patient's breast 18 which is transmitted to monitor 20 as generally indicated by arrow 134.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An apparatus for use in imaging an area of interest within a patient's breast, the area of interest having a width relative to the patient's chest wall, comprising:

source means for transmitting a radiation signal through said area of interest within said patient's breast;

receiving means, disposed in opposing relation to said source means with said patient's breast positioned therebetween, for receiving said transmitted radiation signal, said receiving means comprising an active array of detector elements for accumulating electrical charge indicative of said received radiation signal, said active array of detector elements having a width relative to said patient's chest wall which is less than a width of said area of interest within said patient's breast;

scanning means for scanning said receiving means by moving said active array of detector elements in a direction generally parallel to said patient's chest wall across said width of said area of interest within said patient's breast during an exposure period wherein said radiation signal is transmitted through said patient's breast; and processing means for sequentially reading out said accumulated electrical charge from said active array of detector elements at increments relative to the scan of said receiving means across said area of interest within said patient's breast during said exposure period thereby obtaining incremental imaging data, and for providing a composite image of said area of interest within said patient's breast based on said incremental imaging data.

2. The apparatus of claim 1, wherein said source means comprises collimator means for collimating said radiation signal such that said radiation signal transmitted through said patient's breast is a narrow generally fan shaped beam of radiation wherein said fan shaped beam has a narrow width relative to said patient's chest wall and said apparatus further comprises means for scanning said beam across said area of interest within said patient's breast.

3. The apparatus of claim 1, wherein said radiation signal transmitted through said patient's breast has a length at least as great as a length of said patient's breast.

4. The apparatus of claim 1, wherein at least one of said source means and said receiving means is mounted on a pivotable pendulum and said scanning means comprises means for pivoting said pendulum.

5. The apparatus of claim 1, wherein said source means and said receiving means are mounted on a pendulum which is pivotable about a pivot axis and said scanning means comprises:

a motor; and transmission means for transmitting power from said motor for pivoting said pendulum, said transmission means including a member which is rotatable about said pivot axis.

6. The apparatus of claim 5, wherein said transmission means further comprises:

a pulley rotatably mounted on an axis separate from said pivot axis; and a belt for driving said pulley in a direction generally parallel to said patient's chest wall.

7. The apparatus of claim 1, wherein said scanning means comprises a steel belt.

8. The apparatus of claim 1, wherein said active array of detector elements generally corresponds to a cross-section of said transmitted radiation signal.

9. The apparatus of claim 1, wherein said receiving means comprises at least one phosphorescent screen and fiber optic means for coupling said phosphorescent screen and said active array of detector elements.

10. The apparatus of claim 1, wherein said processing means is operative for storing imaging information based on said accumulated electrical charge relating to a plurality of scan positions and for using said stored imaging information for forming a composite image of said area of interest within said patient's breast.

11. The apparatus of claim 1, further comprising encoding means for encoding positional information regarding said receiving means relative to a scan across said area of interest within said patient's breast.

12. The apparatus of claim 11, wherein said width of said active array of detector elements is defined by a plurality of rows of detector elements, and said apparatus further comprises shifting means, operatively associated with said encoding means, for shifting electrical charge across said width of said active array.

13. The apparatus of claim 1, further comprising filter support means, disposed between said source means and said patient's breast, for supporting at least first and second radiation filters, wherein said first filter has performance characteristics different than that of said second filter.

14. The apparatus of claim 13, wherein said filter support means is moveable relative to said source means so as to selectively position either said first filter or said second filter in a path of said imaging signal.

15. The apparatus of claim 13, wherein said filter support means is adapted for supporting said first filter in a first position relative to said source means corresponding to a first portion of said area of interest within said patient's breast and for supporting said second filter in a second position relative to said source means corresponding to a second portion of said area of interest within said patient's breast.

16. An apparatus for use in imaging a selected region of a patient's body, comprising:

source means for transmitting a radiation signal through said selected region of said patient's body;

receiving means, disposed in opposing relation to said source means with said selected region of said patient's body positioned therebetween, for receiving said radiation signal transmitted through said selected region of said patient's body, said receiving means comprising an active array of detector elements adapted for accumulating electrical charge indicative of said received radiation signal, thereby yielding imaging information;

scanning means for scanning said receiving means relative to said selected region of said patient's body;

encoding means for providing an encoder signal indicative of a scanning motion relative to a scan of said receiving means across said selected region of said patient's body;

read out means, employing said encoder signal, for reading out said accumulated electrical charge from said active array of detector elements so as to provide a read out signal; and processing means, employing said read out signal, for providing an image of said selected region of said patient's body, wherein said processing means integrates said imaging information obtained over the course of a scan of said receiving means using said encoder signal to yield a composite image of said selected region of said patient's body.

17. The apparatus of claim 16, wherein at least one of said source means and said receiving means is mounted on a pivotable pendulum and said scanning means comprises means for pivoting said pendulum.

18. The apparatus of claim 15, wherein said receiving means is mounted on a pendulum which is pivotable about a pivot axis and said scanning means comprises:

a motor; and transmission means for transmitting power from said motor for pivoting said pendulum, said means for transmitting including a member which is rotatable about said pivot axis.

19. The apparatus of claim 16, wherein said scanning means comprises a steel belt.

20. The apparatus of claim 16, further comprising filter support means, disposed between said source means and said selected region of said patient's body, for supporting at least first and second radiation filters, wherein said first filter has performance characteristics different than that of said second filter.

21. An apparatus for use in imaging an area of interest within a patient's body, comprising:

transmitting means for transmitting an imaging signal through said area of interest within said patient's body;

receiving means, disposed in opposing relation to said transmitting means with said area of interest within said patient's body positioned therebetween, for receiving said imaging signal transmitted through said area of interest within said patient's body;

collimator means for collimating said imaging signal into a narrow beam, said narrow beam having a longitudinal length and a transverse width, wherein said width is substantially less than said length and less than a width of said area of interest within said patient's body;

positioning means for positioning said collimator means such that said narrow beam is moveable across to said area of interest within said patient's body;

filter support means, for supporting at least first and second radiation filters, wherein said first filter has performance characteristics different than that of said second filter, said filter support means being supportably connected to said collimator means to provide for a first positioning of said filter support means relative to said area of interest in unison with said positioning of said collimator means by said positioning means and a second positioning of said filter support means in a transverse direction relative to said collimator means; and selection means, operatively associated with said filter support means, for selectively positioning one of said first filter or said second filter in a path of said narrow beam by transversely moving at least one of said first and second filters relative to said collimator means, wherein said apparatus allows for filter selection and movement of said narrow beam across said area of interest within said patient's body.

22. The apparatus of claim 21, further comprising user interface means for allowing a user co direct said selection means so as to position either said first filter or said second filter in a path of said imaging signal.

23. The apparatus of claim 21, wherein said selection means is operative for receiving feedback regarding a characteristic of said area of interest within said patient's body and for selectively positioning either said first filter or said second filter in a path of said imaging signal based on said feedback.

24. The apparatus of claim 21, wherein said area of interest is located within said patient's breast, further comprising:

compression means for compressing said patient's breast; and sensing means for sensing one of the compressed thickness of said patient's breast and the compression pressure applied to said patient's breast.

25. The apparatus of claim 21, wherein said selection means is operative for receiving information regarding a test imaging signal exposure of said patient's body and using said received information to selectively position either said first filter or said second filter in a path of said imaging signal.

26. An apparatus for use in imaging an area of interest within a patient's body, comprising:

source means for transmitting a radiation signal through said selected region of said patient's body;

receiving means, disposed in opposing relation to said source means with said selected region of said patient's body positioned therebetween, for receiving said radiation signal transmitted through said selected region of said patient's body; and filter support means for simultaneously supporting a first filter element in a first position relative to said source means corresponding to a first portion of said area of interest within said patient's body and a second filter element in a second position relative to said source means corresponding to a second portion of said area of interest within said patient's body, said second filter element having filtering characteristics different than said first filter element, wherein a first portion of said radiation signal passes through said first filter element and a second portion of said radiation signal passes through said second filter element.

27. The apparatus of claim 26, wherein said area of interest is located within said patient's breast, and said filter support means is adapted for supporting said first filter element in said first position such that said first filter element interacts with said first portion of said radiation signal for imaging an anterior portion of said patient's breast.

* * * * *